United States Patent
Igawa et al.

(10) Patent No.: US 10,907,091 B2
(45) Date of Patent: Feb. 2, 2021

(54) ORGANIC COMPOUND AND ELECTROCHROMIC ELEMENT

(71) Applicant: CANON KABUSHIKI KAISHA, Tokyo (JP)

(72) Inventors: Satoshi Igawa, Fujisawa (JP); Kenji Yamada, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 154 days.

(21) Appl. No.: 16/261,756

(22) Filed: Jan. 30, 2019

(65) Prior Publication Data

US 2019/0241798 A1 Aug. 8, 2019

(30) Foreign Application Priority Data

Feb. 6, 2018 (JP) .................................. 2018-019294
Jan. 15, 2019 (JP) .................................. 2019-004490

(51) Int. Cl.
*G02F 1/153* (2006.01)
*C09K 9/02* (2006.01)
(Continued)

(52) U.S. Cl.
CPC .............. *C09K 9/02* (2013.01); *C07D 471/04* (2013.01); *E06B 9/24* (2013.01); *G02F 1/1516* (2019.01);
(Continued)

(58) Field of Classification Search
CPC . C07D 401/04; C07D 409/14; C07F 9/65583; C07F 9/5765; C07F 9/65616;
(Continued)

(56) References Cited

U.S. PATENT DOCUMENTS 6,020,987 A 2/2000 Baumann et al.
9,701,671 B2 7/2017 Igawa et al.
(Continued)

FOREIGN PATENT DOCUMENTS

JP 2001-519922 A 10/2001
JP 2017-165708 A 9/2017
(Continued)

OTHER PUBLICATIONS

Extended European Search Report in European Application No. 19155218.1 (dated May 9, 2019).

*Primary Examiner* — Mahidere S Sahle
(74) *Attorney, Agent, or Firm* — Venable LLP

(57) ABSTRACT

An organic compound according to one embodiment of the present invention is an organic compound represented by general formula (1).

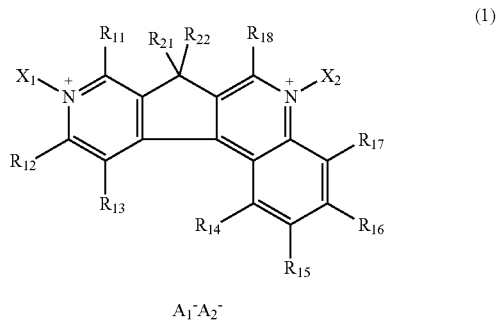

Each of $X_1$ and $X_2$ is an alkyl group or the like that may have a substituent. Each of $R_{11}$ to $R_{18}$ is a hydrogen atom, an alkyl group that may have a substituent, or the like. Each of $R_{21}$
(Continued)

and $R_{22}$ is a hydrogen atom, an alkyl group that may have a substituent, or the like. $A_1$- and $A_2$- independently represent a monovalent anion, respectively.

13 Claims, 7 Drawing Sheets

(51) Int. Cl.
- *G02F 1/1516* (2019.01)
- *C07D 471/04* (2006.01)
- *E06B 9/24* (2006.01)
- *G02F 1/163* (2006.01)
- *G03B 11/00* (2006.01)
- *E06B 3/67* (2006.01)

(52) U.S. Cl.
CPC .............. *G02F 1/163* (2013.01); *G03B 11/00* (2013.01); *C09K 2211/1018* (2013.01); *E06B 3/6722* (2013.01); *E06B 2009/2464* (2013.01); *G02F 2001/1635* (2013.01)

(58) Field of Classification Search
CPC .... C07F 9/6584; G02F 1/1503; G02F 1/1516; G02F 1/15; G02F 1/163; G02F 1/1523; G02F 1/1524; G02F 2001/1518
USPC ........................................................ 359/273
See application file for complete search history.

(56) References Cited

U.S. PATENT DOCUMENTS

| | | |
|---|---|---|
| 2016/0246152 A1 | 8/2016 | Igawa et al. |
| 2019/0002758 A1 | 1/2019 | Igawa et al. |

FOREIGN PATENT DOCUMENTS

| | | |
|---|---|---|
| WO | 98/44384 A1 | 10/1998 |
| WO | 2011/046222 A1 | 4/2011 |
| WO | 2017/154681 A1 | 9/2017 |

ORGANIC COMPOUND AND ELECTROCHROMIC ELEMENT

BACKGROUND

Field of the Disclosure

The present invention relates to an organic compound and an electrochromic element, an optical filter, and lens unit, an imaging apparatus, and a window member that have the organic compound.

Description of the Related Art

An electrochromic element is an element having a pair of electrodes and an electrochromic layer arranged between the pair of electrodes. By applying a voltage between the pair of electrodes, it is possible to adjust the amount of a light passing through the electrochromic layer. As electrochromic (hereafter, which may be simply referred to as "EC") material in which the property of an optical absorption of a substance (a chromatic state or a light transmittance) changes due to electrochemical oxidation-reduction reaction, various materials such as an inorganic material, a polymer material, an organic low molecular material, or the like are known. With these materials, EC elements have been applied to a dimming mirror of an automobile, an electronic paper, or the like. These devices employ a property of being capable of displaying various color tones in accordance with selection of the material. This implies that, in a use of an EC element, development of materials having various color tones enables a wide range of application. For example, application to a full-color display or the like requires a material colored in cyan, magenta, and yellow. Application to a wider range of application requires coloring materials of various color tones. Further, there is room to improve stability of coloring and achromatizing or repetition durability in a long term use.

Patent Reference 1 (International Publication No. WO2011/046222) discloses an organic compound of pyridine derivatives colored in a reduced state and discloses an electrochromic element colored in cyan, magenta, and yellow. Further, in application of an EC material to a full-color display, a color filter, or the like, it is desirable that the EC material be colored in the same color regardless of a usage environment temperature. Patent Reference 2 (Japanese Patent Application Laid-Open No. 2001-519922) discloses an electrochromic element of various viologen derivatives.

For putting electrochromic elements into practical use, compounds having various properties are needed depending on types or application of applied devices, and the compounds disclosed in Patent References 1 and 2 are insufficient.

SUMMARY

One embodiment of the present invention intends to provide an organic compound that can absorb a light of a range around 500 nm to be colored or achromatized by oxidation-reduction reaction and has a high stability against repeated oxidation-reduction reaction.

One embodiment of the present invention provides an organic compound represented by the following general formula (1).

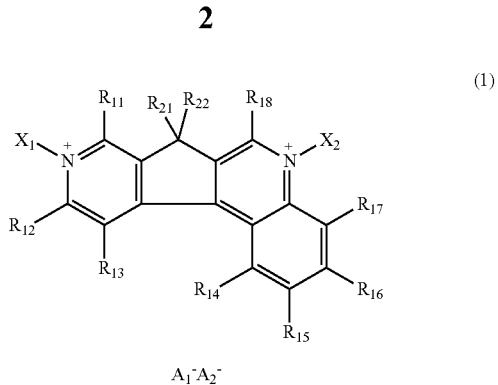

In the general formula (1), $X_1$ and $X_2$ are independently selected from the group consisting of a substituted or unsubstituted alkyl group, a substituted or unsubstituted aryl group, and a substituted or unsubstituted aralkyl group.

$R_{11}$ to $R_{18}$ are independently selected from the group consisting of a hydrogen atom and a substituent, and each substituent represented by the $R_{11}$ to $R_{18}$ is any one of a substituted or unsubstituted alkyl group, a substituted or unsubstituted alkoxy group, a substituted or unsubstituted aryl group, a substituted or unsubstituted heterocyclic group, a halogen atom, and a cyano group.

$R_{21}$ and $R_{22}$ are independently selected from the group consisting of a hydrogen atom and a substituent, and each substituent represented by the $R_{21}$ and $R_{22}$ is any one of a substituted or unsubstituted alkyl group, a substituted or unsubstituted aryl group, and a substituted or unsubstituted aralkyl group.

$A_1^-$ and $A_2^-$ independently represent a monovalent anion.

Further features of the present invention will become apparent from the following description of exemplary embodiments with reference to the attached drawings.

DESCRIPTION OF THE EMBODIMENTS

Organic Compound

Figure 1:
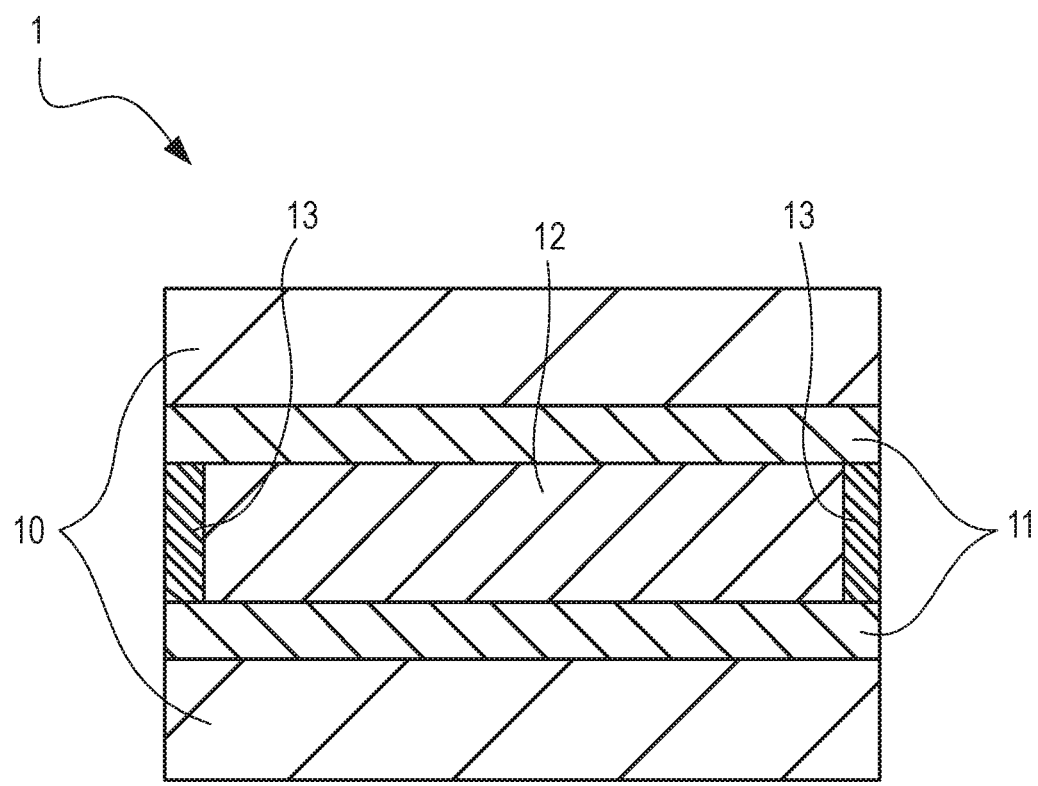
FIG. 1 is a schematic sectional view of an example of an electrochromic element according to an embodiment.

An organic compound according to one embodiment of the present invention is an organic compound having an electrochromic property. The organic compound having an electrochromic property may be referred to as an electrochromic compound. In the present embodiment, an electrochromic compound may be referred to as an EC compound. Further, in the present embodiment, the expression "colored" means that a transmittance at a particular wavelength decreases.

The organic compound according to one embodiment of the present invention is expressed by the following general formula (1).

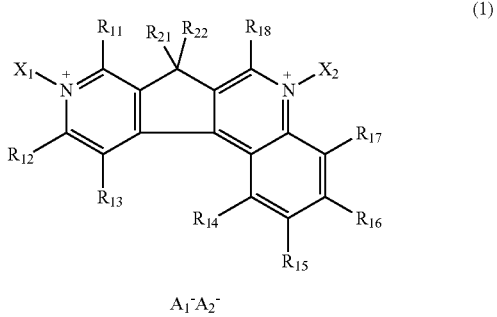

(1)

In the general formula (1), $X_1$ and $X_2$ are independently selected from an alkyl group that may have a substituent, an aryl group that may have a substituent, and an aralkyl group that may have a substituent, respectively. $R_{11}$ to $R_{18}$ are independently selected from a hydrogen atom and a substituent, respectively. Each substituent expressed by the $R_{11}$ to $R_{18}$ is any one of an alkyl group that may have a substituent, an alkoxy group that may have a substituent, an aryl group that may have a substituent, a heterocyclic group that may have a substituent, a halogen atom, and a cyano group. $R_{21}$ and $R_{22}$ are independently selected from a hydrogen atom and a substituent, respectively, and each substituent expressed by the $R_{21}$ and $R_{22}$ is any one of an alkyl group may have a substituent, an aryl group that may have a substituent, and an aralkyl group that may have a substituent. $A_1^-$ and $A_2^-$ independently represent a monovalent anion, respectively.

Each of the alkyl groups expressed by $X_1$ and $X_2$, $R_{11}$ to $R_{18}$, and $R_{21}$ and $R_{22}$ preferably has one to eight carbon atoms, and may be straight-chained, branched-chained, or cyclic. Further, the hydrogen atom may be replaced with a halogen atom, preferably a fluorine atom. Further, the carbon atom included in the alkyl group may be replaced with an ester group or a cyano group. An alkyl group may be, specifically, a methyl group, an ethyl group, a normal propyl group, an isopropyl group, a normal butyl group, a tertiary butyl group, an octyl group, a cyclohexyl group, a trifluoromethyl group, or the like.

Further, the terminal of each alkyl group expressed by $X_1$ and $X_2$ may have an adsorptive group or an acid ester group thereof to be adsorbed to a porous electrode. A specific example of the adsorptive group or the acid ester group thereof may be a carboxyl group and a carboxyl ester group, a sulfonic group and a sulfonic ester group, a phosphonic group and a phosphonic ester, a trialkoxysilyl group, or the like. Moreover, to improve a solubility to an organic solvent, the terminal of the alkyl group may have an ionizable group such as a pyridinium, a quinolinium, or the like.

Each aralkyl group expressed by $X_1$ and $X_2$ and $R_{21}$ and $R_{22}$ may be a benzyl group, a phenethyl group, or the like. The aralkyl group may have a substituent, specifically, may have an alkyl group having one to eight carbon atoms or an alkoxy group having one to eight carbon atoms. The hydrogen atom included in the alkyl group or the alkoxy group may be replaced with a halogen atom, preferably a fluorine atom. Further, when the aralkyl group expressed by $X_1$ and $X_2$ has an alkyl group or an alkoxy group, the terminal thereof may have an adsorptive group or an acid ester group thereof to be adsorbed to a porous electrode, or may have an ionizable group in order to improve solubility to an organic solvent. The specific examples of the adsorptive group or the acid ester group and the ionizable group are the same as the examples listed for the alkyl group expressed by $X_1$ and $X_2$.

Each alkoxy group expressed by $R_{11}$ to $R_{18}$ preferably has one to eight carbon atoms and may be straight-chained, branched-chained, or cyclic. The alkoxy group may be, specifically, a methoxy group, an ethoxy group, an isopropyloxy group, a tertiary butyloxy group, an octyloxy group, a cyclohexyloxy group, a trifluoromethyloxy group, or the like. Further, the hydrogen atom included in the alkoxy group may be replaced with a halogen atom. When replaced with a halogen atom, the halogen atom is preferably a fluorine atom.

Each aryl group expressed by $X_1$ and $X_2$, $R_{11}$ to $R_{18}$, and $R_{21}$ and $R_{22}$ preferably may be a phenyl group, a biphenyl group, a terphenyl group, a fluorenyl group, a naphthyl group, a fluoranthenyl, an anthryl group, a phenanthryl group, a pyrenyl group, a tetracenyl group, a pentacenyl group, a triphenylenyl group, a perylenyl group, or the like. When the aryl group has a substituent, the substituent may have at least any of a halogen atom, an alkyl group having one to eight carbon atoms, and an alkoxy group having one to eight carbon atoms. The hydrogen atom included in the alkyl group or the alkoxy group may be replaced with a halogen atom, preferably a fluorine atom. Further, when the aryl group expressed by $X_1$ and $X_2$ has an alkyl group or an alkoxy group, the terminal thereof may have an adsorptive group or an acid ester group thereof to be adsorbed to a porous electrode, or may have an ionizable group in order to improve solubility to an organic solvent. The specific examples of the adsorptive group or the acid ester group and the ionizable group thereof are the same as the examples listed for the alkyl group expressed by $X_1$ and $X_2$.

Each heterocyclic group expressed by $R_{11}$ to $R_{18}$ may be a thienyl group, a pyrrolyl group, a pyridyl group, an oxazolyl group, an oxadiazolyl group, a thiazolyl group, a thiadiazolyl group, a terthienyl group, a quinolyl group, an isoquinolyl group, a carbazolyl group, or the like. When the heterocyclic group has a substituent, the substituent may have at least any of an alkyl group having one to eight carbon atoms and an alkoxy group having one to eight carbon atoms. The hydrogen atom included in the alkyl group or the alkoxy group may be replaced with a halogen atom, preferably a fluorine atom.

Each halogen atom expressed by $R_{11}$ to $R_{18}$ may be a fluorine, a chlorine, a bromine, an iodine, or the like.

$A_1^-$ and $A_2^-$ may be the same or different and selected from anions such as $PF_6^-$, $ClO_4^-$, $BF_4^-$, $AsF_6^-$, $SbF_6^-$, $CF_3O_3^-$, $(CF_3SO_2)_2N^-$, or the like or halogen anions such as Br⁻, Cl⁻, I⁻, or the like and may be preferably any of $PF_6^-$, $ClO_4^-$, $BF_4^-$, $CF_3SO_3^-$, or $(CF_3SO_2)_2N^-$. More preferably, $A_1^-$ and $A_2^-$ are the same anion.

While a method for producing the organic compound according to one embodiment of the present invention is not particularly limited, the organic compound may be produced by a method illustrated below, for example. When $X_1$ and $X_2$ are the alkyl group and the aralkyl group, the organic compound can be obtained by a reaction of an organic compound expressed by the flowing general formula (2) with a halogen compound in a predetermined solvent and then an anion-exchange reaction with a salt containing a desired anion in a predetermined solvent. When $X_1$ and $X_2$ are the aryl group, the organic compound can be obtained by a reaction with 2,4-dinitrophenyl halide, synthesis of 2,4-dinitrophenyl-2,7'-diazafluorenium, then a reaction with arylamine, and an anion-exchange reaction with a salt containing an anion in a predetermined solvent. Further, proper selection of the solvent and the reaction temperature allows for a reaction of only one of the imines. By repeating the reaction, it is possible to introduce mutually different substituents for two imines.

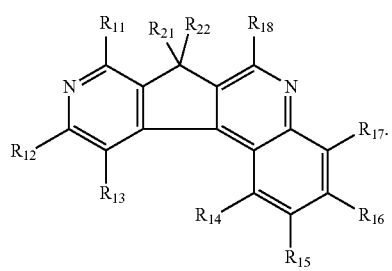

(2)

While a producing method of the organic compound expressed by the above general formula (2) is not particularly limited, the organic compound can be produced according to a producing method illustrated below, for example. $R_{11}$ to $R_{18}$ and $R_{21}$ and $R_{22}$ within the synthesis route represent hydrogen atoms or substituents in a similar manner to general formula (1), and X represents a halogen atom.

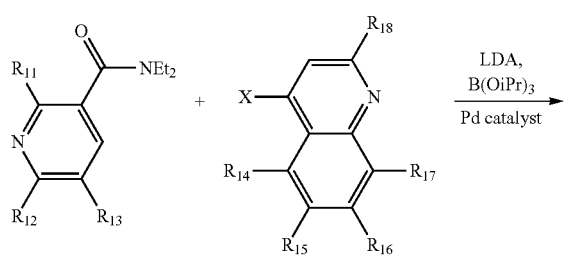

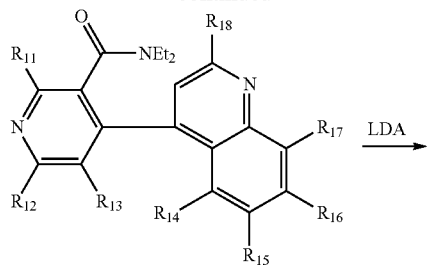

Intermediate 1

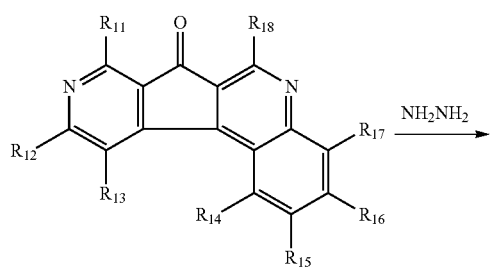

Intermediate 2

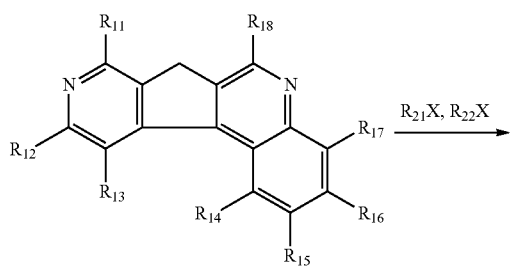

Intermediate 3

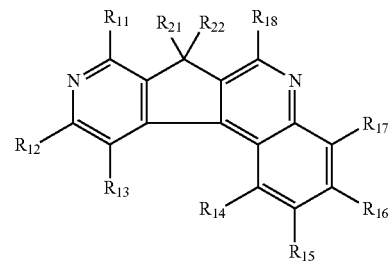

The intermediate 1 can be synthesized by coupling of N,N-diethylnicotinamide derivative and 4-halogeno-quinoline derivative. The intermediate 2 can be synthesized by a cyclization reaction of the intermediate 1 using the lithium diisopropylamide (LDA). Furthermore, the intermediate 3 can be synthesized by a Wolff-Kishner reduction of the intermediate 2. The organic compound expressed by general formula (2) can be synthesized by a reaction of the intermediate 3 and a desired halogen substance under the presence of a base.

Specific structural formulae of the organic compound according to one embodiment of the present invention will be illustrated below as examples. However, the compound according to the present invention is not limited thereto.

7
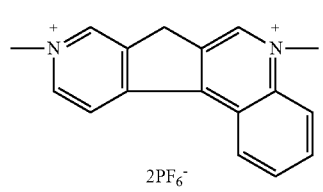
A-1
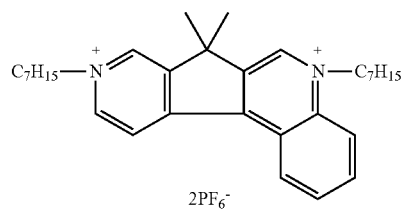
A-2
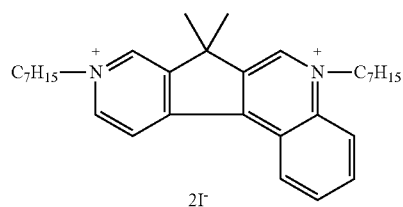
A-3
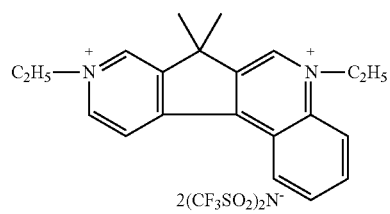
A-4
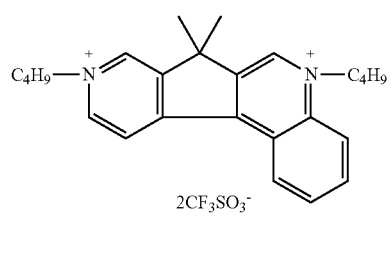
A-5
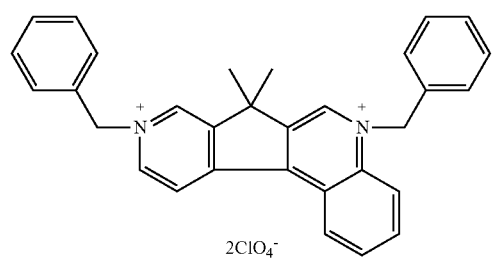
A-6
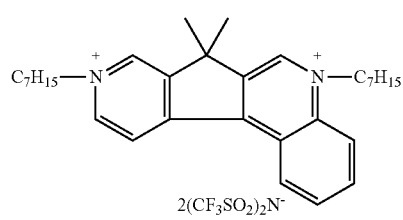
A-7
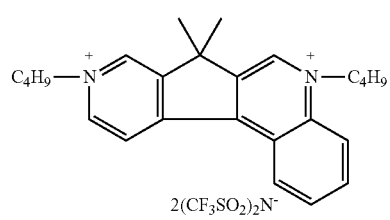
A-8
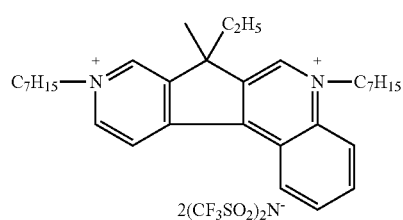
A-9
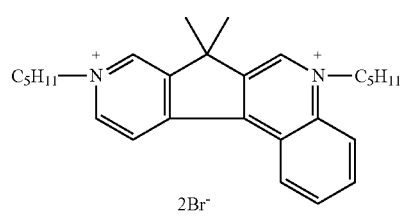
A-10
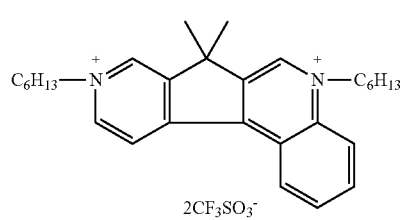
A-11
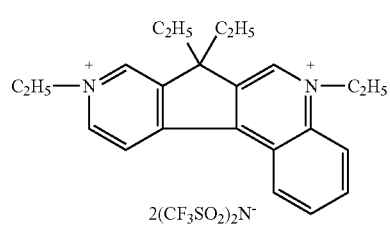
A-12
8

A-13
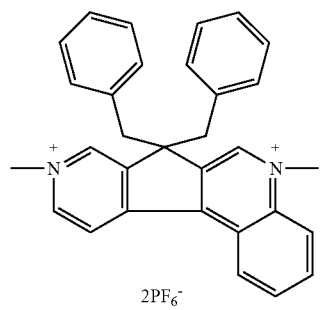
2PF6⁻
A-14
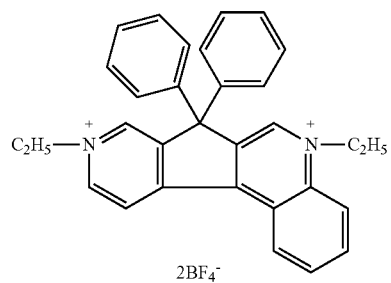
2BF4⁻
A-15
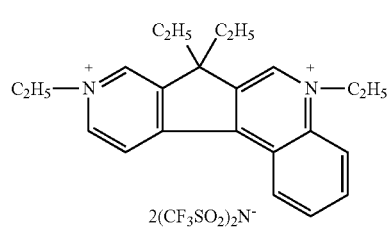
2(CF3SO2)2N⁻
A-16
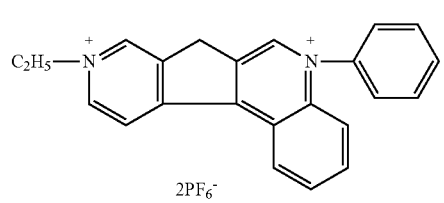
2PF6⁻
A-17
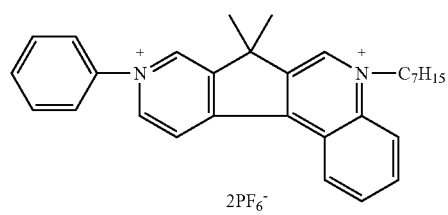
2PF6⁻
A-18
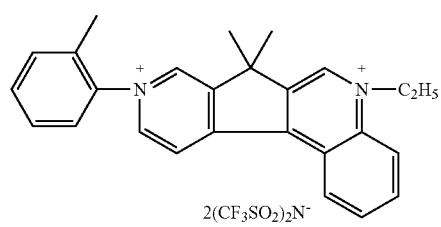
2(CF3SO2)2N⁻
A-19
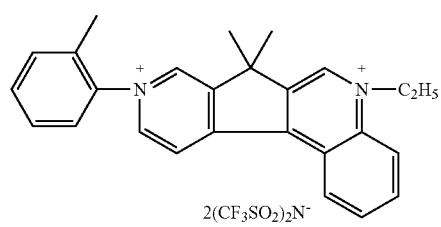
2(CF3SO2)2N⁻
A-20
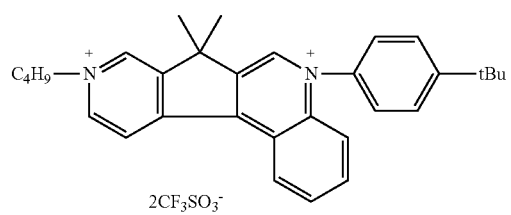
2CF3SO3⁻
A-21
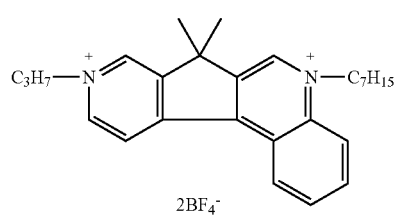
2BF4⁻
A-22
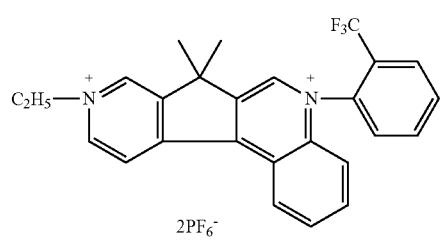
2PF6⁻
A-23
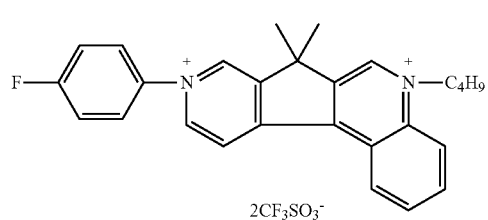
2CF3SO3⁻
A-24
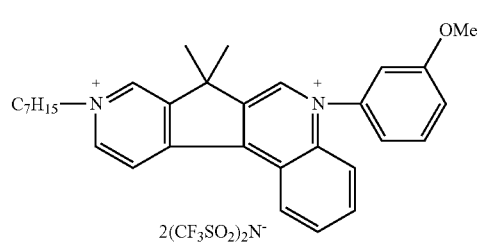
2(CF3SO2)2N⁻

-continued
A-25
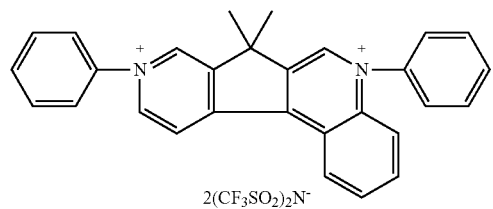
A-26
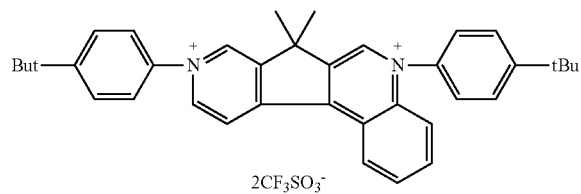
A-27
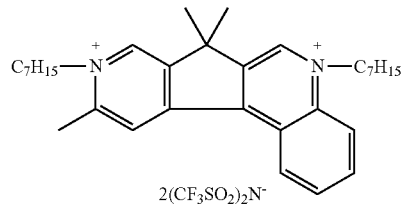
A-28
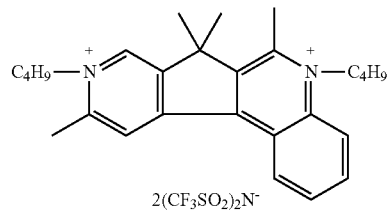
A-29
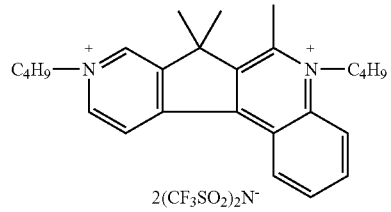
A-30
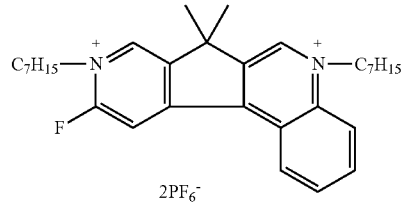
A-31
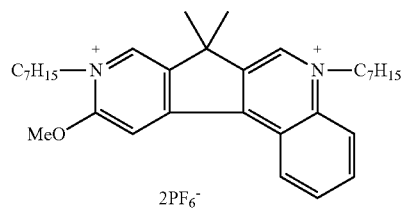
A-32
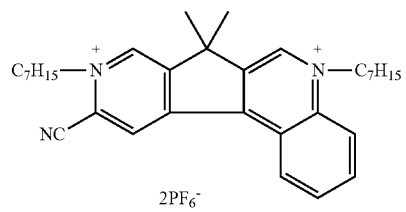
A-33
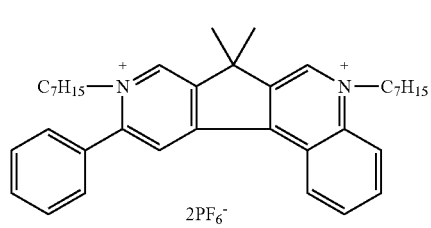
A-34
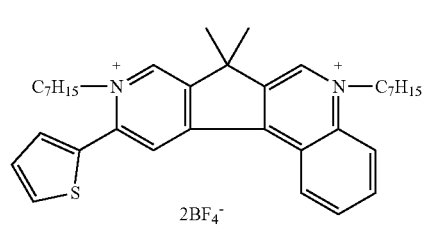
A-35
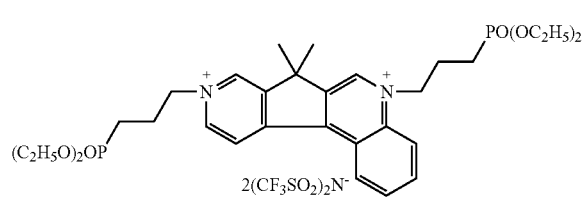
A-36
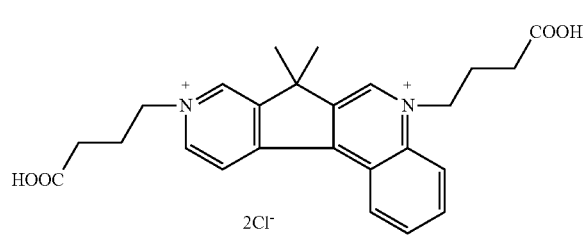

-continued

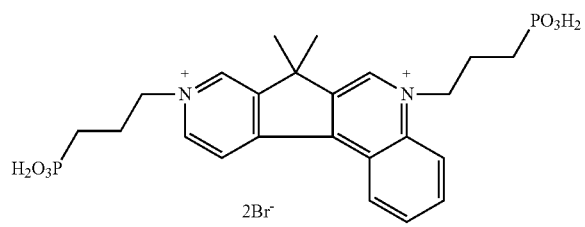
A-37

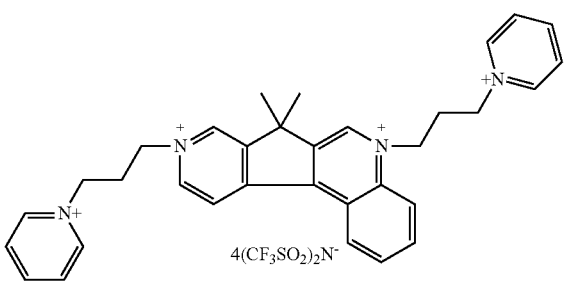
A-38

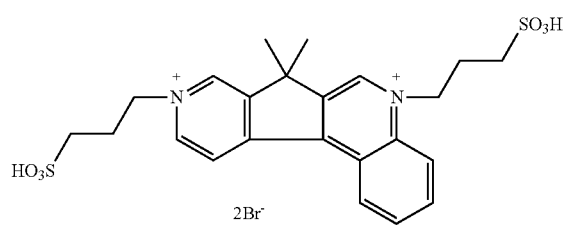
A-39

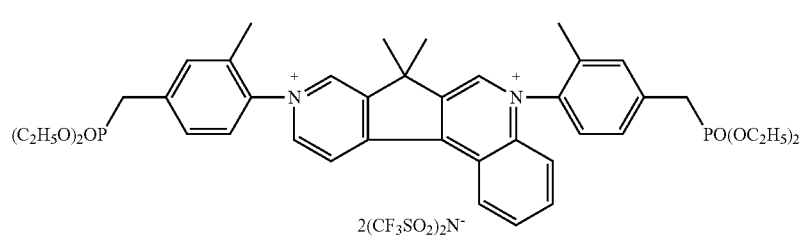
A-40

Because of having the structure expressed by general formula (1), the organic compound according to one embodiment of the present invention is a compound having a high transmittance when solved in a solvent. Further, an organic compound according to one embodiment of the present invention is a compound colored in a reduced state. The compound colored in a reduced state is a compound in which the transmittance of a visible light in a reduced state is lower than the transmittance of the visible light in an oxidation state. The organic compound according to one embodiment of the present invention is an electrochromic material that exhibits stable coloring against the ambient temperature and can be used for an EC element and an optical filter, a lens unit, an imaging apparatus, and the like using the EC element. The organic compound according to one embodiment of the present invention is a compound colored in a reduced state in such a way, which can absorb a light of a range around 500 nm by oxidation-reduction reaction and be colored or achromatized and has a high stability against repetition of oxidation-reduction reaction.

EC Element

The EC compound according to one embodiment of the present invention can be used as an electrochromic layer of an electrochromic element. The electrochromic element according to the present embodiment will be described below with reference to the drawings. In the following, the electrochromic element may be denoted as an EC element.

The EC element 1 of FIG. 1 is an EC element having a pair of transparent electrodes 11 and an EC layer 12 having an electrolyte and an EC compound according to the present invention arranged between the pair of transparent electrodes 11. The pair of transparent electrodes 11 interposes a spacer 13 and thereby has a constant distance between the transparent electrodes 11. In the EC element 1, the pair of transparent electrodes 11 are arranged between a pair of transparent substrates 10.

The EC layer 12 has an EC compound according to one embodiment of the present invention. The EC layer 12 may have a layer consisting of an EC compound and a layer consisting of an electrolyte. Further, the EC layer 12 may be provided as a solution having an EC compound and an electrolyte. The EC element according to the present embodiment is preferably an EC element in which the EC layer 12 is a solution.

Next, members forming the EC element 1 according to the present embodiment will be described. The electrolyte is not particularly limited as long as it is an ion-dissociation salt and exhibits good solubility to a solvent and high compatibility in a solid electrolyte. In particular, an electro-donating electrolyte is preferable. These electrolytes may also be referred to as a support electrolyte. The electrolyte may be, for example, an inorganic ionic salt such as various an alkaline metal salt, an alkaline earth metal salt, or the like, a quaternaty ammonium salt, a cyclic quaternaty ammonium salt, or the like. Specifically, the electrolyte may be an alkaline metal salt or the like of Li, Na, or K such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, or $KCl$ and a quaternaty ammonium salt and a cyclic quaternaty ammonium salt such as $(CH_3)_4NBF_4$, $(C_2H_5)_4NBF_4$, $(n\text{-}C_4H_9)_4NBF_4$, $(n\text{-}C_4H_9)_4NPF_6$, $(C_2H_5)_4NBr$, $(C_2H_5)_4NClO_4$, or $(n\text{-}C_4H_9)_4NClO_4$, or the like.

While not particularly limited as long as it can solve the EC compound or the electrolyte, a solvent in which the EC compound and the electrolyte are solved is preferably a solvent having a polarity, in particular. Specifically, the solvent may be water or an organic polar solvent such as methanol, ethanol, propylenecarbonate, ethylenecarbonate, dimethylsulfoxide, dimethoxyethane, γ-butyrolactone, γ-valerolactone, sulfolane, dimethylformamide, dimethoxyethane, tetrahydrofuran, acetonitrile, propionenitrile, benzonitrile, dimethylacetamide, methylpyrrolidinone, dioxolane, or the like.

Furthermore, for the EC layer 12, a material having a high viscosity further containing a polymer or a gelling agent or a gelled material, or the like can be used. The polymer is not particularly limited and may be, for example, polyacrylonitrile, carboxymethylcellulose, polyvinyl chloride, polyethyleneoxide, polypropyleneoxide, polyurethane, polyacrylate, polymethacrylate, polyamide, polyacrylamide, polyester, Nafion (registered trademark), or the like.

Next, a transparent substrate 10 and a transparent electrode 11 will be described. For the transparent substrate 10, a colorless or colored glass, a tempered glass, or the like may be used, and in addition, a colorless or colored transparent resin may be used, for example. Note that the term "transparent" in the present embodiment indicates that the transmittance of a visible light is 90% or higher. Specifically, polyethyleneterephthalate, polyethylenenaphthalate, polynorbornene, polyamide, polysulfone, polyethersulfone, polyetheretherketone, polyphenylenesulfide, polycarbonate, polyimide, polymethylmethacrylate, or the like may be used.

The material of the transparent electrode 11 may be, for example, a metal or a metal oxide such as indium tin oxide alloy (ITO), fluorine doped tin oxide (FTO), tin oxide (NESA), indium zinc oxide (IZO), silver oxide, vanadium oxide, molybdenum oxide, gold, silver, platinum, copper, indium, or chromium, a silicon-based material such as polycrystal silicon, or amorphous silicon, or a carbon material such as carbon black, graphite, or glassy carbon, or the like. Further, a conductive polymer whose conductivity has been improved by a doping process or the like, for example, polyaniline, polypyrrole, polythiophene, polyacetylene, polyparaphenylene, a complex of polyethylenedioxythiophene (PEDOT) and polystyrene sulfonate, or the like may be preferably used.

Furthermore, a porous electrode may be provided on the transparent electrode 11. The porous electrode may be preferably a material having a large surface area having a porous shape, a rod shape, a wire shape, or the like having fine holes on the surface and inside. The material of the porous electrode may be, for example, a metal, a metal oxide, a carbon, or the like. More preferably, a metal oxide such as titanium oxide, tin oxide, iron oxide, strontium oxide, tungsten oxide, zinc oxide, tantalum oxide, vanadium oxide, indium oxide, nickel oxide, manganese oxide, or cobalt oxide may be used.

The spacer 13 is arranged between the pair of transparent electrodes 11 and provides a space in which the EC layer 12 having the EC compound according to one embodiment of the present invention is to be accommodated. Specifically, a polyimide, a polytetrafluoroethylene, a fluorine rubber, an epoxy resin, or the like can be used. This spacer 13 enables the distance between the transparent electrodes 11 of the EC element 1 to be maintained.

The EC element 1 according to the present embodiment may have a liquid inlet formed by the pair of electrodes and the spacer. After a composition having the EC compound is injected and sealed from the liquid inlet, the inlet is covered by a seal member and further sealed by an adhesive agent, and thereby an element can be obtained. The seal member is also responsible for separation of the adhesive agent and the EC compound so as not to contact with each other. While the shape of the seal member is not particularly limited, a tapered shape such as a wedge is preferable.

The formation method of the EC element 1 according to the present embodiment is not particularly limited, and a method injecting a liquid containing the EC compound prepared in advance by a vacuum injection method, an air injection method, a meniscus method, or the like into a gap provided between the pair of electrode substrates can be used.

The EC element 1 according to the present embodiment may have the organic compound according to one embodiment of the present invention and another organic compound (second organic compound) which is of a different type from the above organic compound. A single type or multiple types of the second organic compound may be used, and a compound colored in an oxidation state, a compound colored in a reduced state, or a compound having both such properties may be used. Since the organic compound according to one embodiment of the present invention is a compound colored in the reduced state, the second organic compound is preferably a compound colored in an oxidation state. A compound colored in an oxidation state is a compound in which the transmittance of a visible light in an oxidation state is lower than the transmittance of a visible light in a reduced state.

The organic compound according to one embodiment of the present invention can exhibit a desired color as the EC element in combination with a coloring material of another color. Another type of organic compound when colored preferably has an absorption wavelength ranging from 400 nm to 800 nm, more preferably from 420 nm to 700 nm. Having the absorption wavelength in a particular range means that the peak of the absorption spectral needs to be in the particular range. By combining the organic compound according to one embodiment of the present invention and a plurality of other materials, it is also possible to fabricate the EC element 1 that absorbs a light within the entire visible range and is colored in black.

The second organic compound according to the present embodiment may be the following compounds, for example. The compound colored in the oxidation state may be a phenazine compound such as 5,10-dihydro-5,10-dimethylphenazine or 5,10-dihydro-5,10-diethylphenazine, a metallocene compound such as ferrocene, tetra-t-butylferrocene, or titanocene, a phenylenediamine compound such as N,N',N,N'-tetramethyl-p-phenylene diamine, a pyrazoline compound such as 1-phenyl-2-pyrazoline, or the like.

The compound colored in a reduced state may be a viologen compound such as N,N'-diheptyl bipyridinium diperchlorate, N,N'-diheptyl bipyridinium ditetrafluoroborate, N,N'-diheptyl bipyridinium dihexafluorophosphate, N,N'-diethyl bipyridinium diperchlorate, N,N'-diethyl bipyridinium ditetrafluoroborate, N,N'-diethyl bipyridinium dihexafluorophosphate, N,N'-dibenzyl bipyridinium diperchlorate, N,N'-dibenzyl bipyridinium ditetrafluoroborate, N,N'-dibenzyl bipyridinium dihexafluorophosphate, N,N'-diphenyl bipyridinium diperchlorate, N,N'-diphenyl bipyridinium ditetrafluoroborate, or N,N'-diphenyl bipyridinium dihexafluorophosphate, an anthraquinone compound such as 2-ethyl anthraquinone, 2-t-butyl anthraquinone, or octamethyl anthraquinone, a ferrocenium salt compound such as ferrocenium tetrafluoroborate or ferrocenium hexafluorophosphate, a styryl compound, or the like.

The second organic compound is preferably any of the phenazine compound, a metallocene compound, a phenylenediamine compound, and a pyrazoline compound among the above compounds.

It is possible to confirm that the compound contained in the EC layer 12 included in the EC element 1 according to the present embodiment is contained in the EC element 1 by a known method of extraction and analysis. For example, extraction by chromatography and then analysis by using NMR may be employed. Further, when the electrochromic layer is a solid, TOF-SIMS or the like can be used for analysis.

Application of EC Element

The EC element 1 according to the present embodiment can be used in an optical filter, a lens unit, an imaging apparatus, a window member, or the like.

Optical Filter

The optical filter according to the present embodiment has the EC element 1 and an active element connected to the EC element 1. The active element is an active element that drives the EC element and adjusts the amount of a light passing through the EC element. The active element may be a transistor or an MIM element, for example. The transistor may have an oxide semiconductor such as InGaZnO in the active region.

Figure 2:
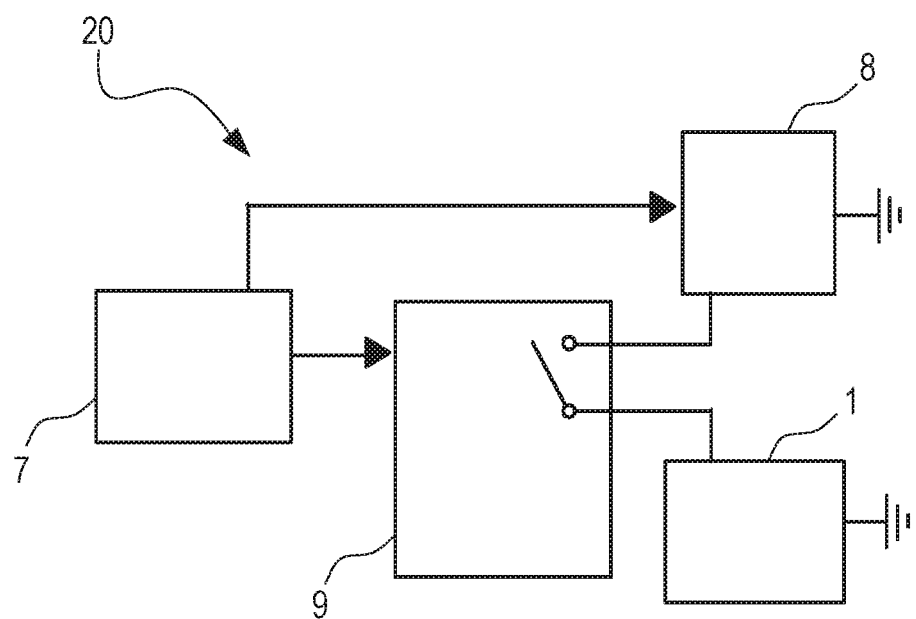
FIG. 2 is a schematic diagram illustrating an example of a drive device connected to the electrochromic element according to the embodiment.

The optical filter has the EC element 1 according to the present embodiment and a drive device connected to the EC element 1. FIG. 2 is a schematic diagram illustrating an example of a drive device 20 of the EC element 1 and the EC element 1 driven by the drive device 20. The drive device 20 of the EC element 1 of the present embodiment has a drive power source 8, a resistor selector 9, and a controller 7.

The drive power source 8 applies, to the EC element 1, a voltage required for the EC material included in the EC layer 12 to cause electrochemical reaction. The drive voltage is more preferably a constant voltage. This is because the absorption spectral may change due to a difference in the oxidation-reduction potential or a difference in the absorptivity of the material when the EC material is consisting of multiple types of materials and thus a constant voltage is preferable. Voltage application from the drive power source 8 is started or an application state is held by a signal from the controller 7, and the application state of a constant voltage is held during a period in which the light transmittance of the EC element 1 is controlled.

The resistor selector 9 switches a resistor 1 (not illustrated) and a resistor 2 (not illustrated), which has a larger resistance than the resistor 1, and connects the selected one in series in the closed circuit including the drive power source 8 and the EC element 1. The resistance of the resistor $R_1$ is preferably at least smaller than the maximum impedance of the element closed circuit, preferably 10Ω or smaller. The resistance of the resistor $R_2$ is preferably larger than the maximum impedance of the element closed circuit, preferably 1 MΩ or less. Note that the resistor $R_2$ may be the air. In such a case, although the closed circuit will be an open circuit in a strict sense, the circuit may be considered as a closed circuit by the air being regarded as the resistor $R_2$.

The controller 7 transmits a switch signal to the resistor selector 9 to control switching of the resistor $R_1$ and the resistor $R_2$.

Lens Unit

The lens unit according to the present embodiment has an imaging optical system having a plurality of lenses and an optical filter having the EC element 1. The optical filter may be provided either between a plurality of lenses or the outside of the lenses. The optical filter is preferably provided on the optical axis of the lens.

Imaging Apparatus

The imaging apparatus according to the present embodiment has an optical filter and a light receiving element that receives a light that has passed through the optical filter. Specifically, the imaging apparatus may be a camera, a video camera, a mobile phone with a camera, or the like. The imaging apparatus may be formed such that a main body having the light receiving element and a lens unit having a lens can be separated from each other. When the main body and the lens unit can be separated from each other in the imaging apparatus, the present invention also includes a form in which an optical filter that is a different body from the imaging apparatus is used when capturing is performed. Note that, in such a case, the arrangement position of the optical filter may be outside the lens unit, between the lens unit and the light receiving element, between a plurality of lenses (when the lens unit has a plurality of lenses), or the like.

Figure 3A:
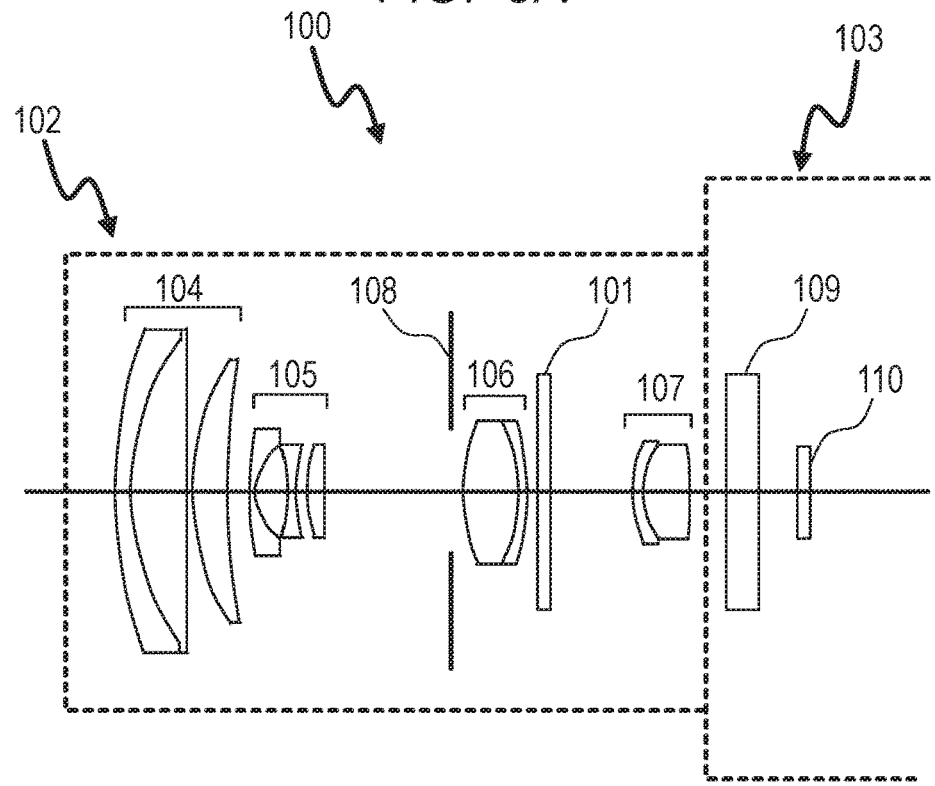
FIG. 3A and FIG. 3B are schematic diagrams illustrating an example of an imaging apparatus according to the embodiment.
Figure 3B:
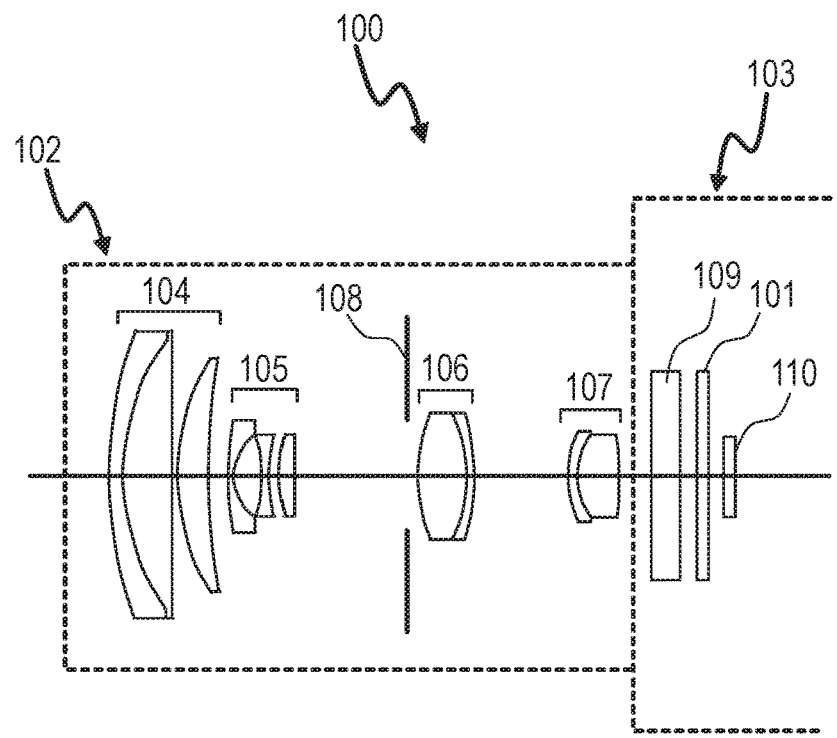

FIG. 3A and FIG. 3B are schematic diagrams illustrating an example of a configuration of an imaging apparatus 100 using the optical filter of the present embodiment.

The imaging apparatus 100 is an imaging apparatus having a lens unit 102 and an imaging unit 103. The lens unit 102 has an optical filter 101 and an imaging optical system having a plurality of lenses or a lens group. The optical filter 101 is the optical filter of the present embodiment described above.

For example, in FIG. 3A, the lens unit 102 represents a zoom lens of a rear focus scheme by which focusing is performed on the rear side of the aperture. Four lens groups: a first lens group 104 having a positive refractive power, a second lens group 105 having a negative refractive power, a third lens group 106 having a positive refractive power, and a fourth lens group 107 of a positive refractive power are provided in this order from an object side. The distance between the second lens group 105 and the third lens group 106 is changed for zooming, and a part of the fourth lens group 107 is moved for focusing.

The lens unit 102 has an aperture 108 between the second lens group 105 and the third lens group 106 and has an optical filter 101 between the third lens group 106 and the fourth lens group 107, for example. The lens groups 104 to 107, the aperture 108, and the optical filter 101 are arranged such that the light passing through the lens unit passes through respective lens groups 104 to 107, the aperture 108, and the optical filter 101, and adjustment of the light amount using the aperture 108 and the optical filter 101 can be performed.

The lens unit 102 is connected so as to be removable with respect to the imaging unit 103 via a mount member (not illustrated).

Note that, while the optical filter 101 is arranged between the third lens group 106 and the fourth lens group 107 within the lens unit 102 in the present embodiment, the arrangement of the imaging apparatus 100 is not limited thereto. For example, the optical filter 101 may be located either on the pre-stage (on the subject side) or on the post stage (on the imaging unit 103 side) of the aperture 108 or may be located on the pre-stage of or the post stage of any one of the first to fourth lens groups 104 to 107 or between the lens groups. Note that, with the optical filter 101 being arranged at the position where a light converges, an advantage of reduction in the area of the optical filter 101 is obtained or the like.

Further, the configuration of the lens unit 102 is not limited to the configuration described above and can be selected as appropriate. For example, other than the rear focus scheme, an inner focus scheme by which focusing is performed on the pre-stage of the aperture may be employed, or other schemes may be employed. Further, a special lens such as a fish eye lens or a macro lens other than a zoom lens may be selected as appropriate.

The imaging unit 103 has a glass block 109 and a light receiving element 110. The glass block 109 is a glass block such as a low-pass filter, a face plate, or a color filter. Further, the light receiving element 110 is a sensor unit that receives a light that has passed through the lens unit and may be an imaging device such as a CCD or a CMOS. Further, an optical sensor such as a photodiode may be used, and those acquiring and outputting information on a light intensity or a wavelength may be used as appropriate.

As illustrated in FIG. 3A, when the optical filter 101 is embedded in the lens unit 102, the drive device may be arranged inside the lens unit 102 or may be arranged outside the lens unit 102. When arranged outside the lens unit 102, the drive device is connected to the EC element 1 inside the lens unit 102 through a wiring for drive control.

Further, in the configuration of the imaging apparatus 100 described above, the optical filter 101 is arranged inside the lens unit 102. However, the present invention is not limited to this form and may be arranged in any form as long as the optical filter 101 is arranged at a suitable portion inside the imaging apparatus 100 and the light receiving element 110 is arranged so as to receive a light that has passed through the optical filter 101.

For example, as illustrated in FIG. 3B, the imaging unit 103 may have the optical filter 101. FIG. 3B is a diagram illustrating a configuration of another example of the imaging apparatus of the present embodiment, which is a schematic diagram of a configuration of an imaging apparatus having an optical filter in the imaging unit 103. In FIG. 3B, the optical filter 101 is arranged on the immediate pre-stage of the light receiving element 110, for example. When the optical filter 101 is built in the imaging apparatus, since the connected lens unit 102 is not required to have the optical filter 101, a dimmable imaging apparatus using the existing lens unit 102 can be configured.

The imaging apparatus 100 of the present embodiment is applicable to a product having a combination of a light amount adjuster and a light receiving element. For example, the imaging apparatus 100 can be used in a camera, a digital camera, a video camera, or a digital video camera and can be also applied to a product embedding an imaging apparatus therein such as a mobile phone or a smartphone, a PC, or a tablet.

According to the imaging apparatus 100 of the present embodiment, with the use of the optical filter 101 as a dimming member, a dimming amount can be suitably changed by using a single filter, and advantages of the reduced number of components and space saving are obtained.

Window Member

The window member according to the present embodiment has the EC element 1 and an active element connected to the EC element 1. The active element is an active element that drives the EC element and adjusts the amount of a light passing through the EC element. The active element may be, for example, a transistor or an MIM element. The transistor may have an oxide semiconductor such as InGaZnO in the active region.

Figure 4A:
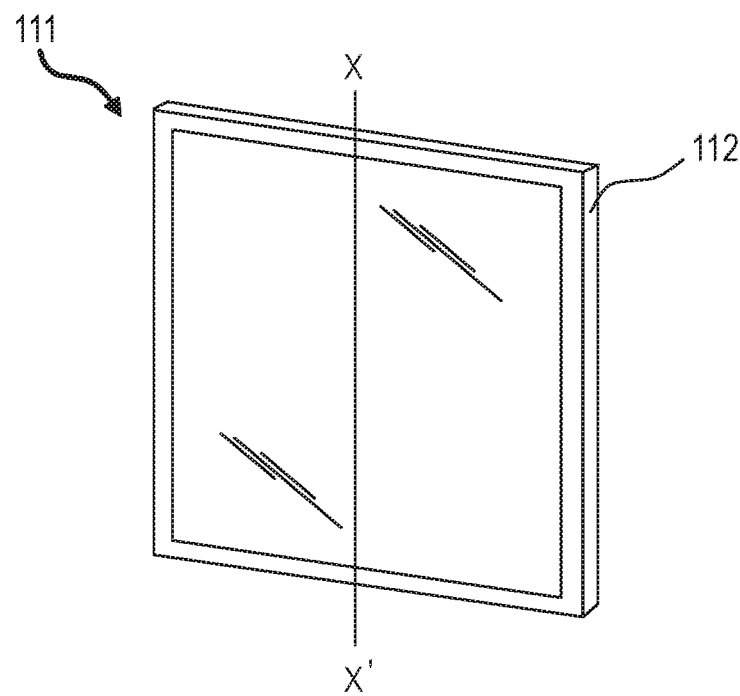
FIG. 4A and FIG. 4B are schematic diagrams illustrating an example of a window member according to the embodiment.
Figure 4B:
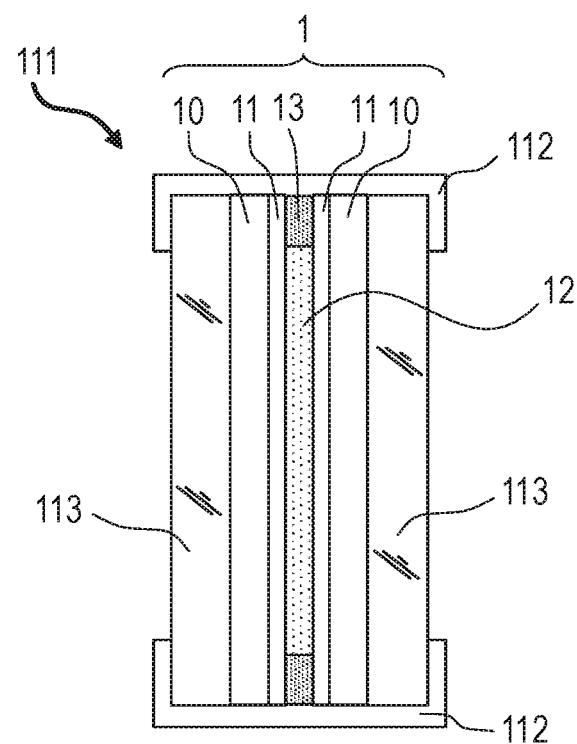

FIG. 4A is a perspective view illustrating a dimming window as a window member using the EC element 1 according to the present embodiment, and FIG. 4B is a schematic diagram illustrating a sectional view taken along X-X' of FIG. 4A. The dimming window 111 of the present embodiment includes the EC element 1 (optical filter), a transparent plate 113 that holds the EC element 1, and a frame 112 that surrounds and integrates the entirety. The EC element 1 has a drive device (not illustrated), which may be integrated inside the frame 112 or may be arranged outside the frame 112 and connected to the EC element 1 through a wiring.

The material of the transparent plate 113 is not particularly limited as long as it has a high optical transmittance and is preferably a glass material when taking usage as a window into consideration. Any material may be employed to the frame 112, and those covering at least a part of the EC element 1 and having an integrated form in general may be considered as the frame. While the EC element 1 is a separate component from the transparent plate 113 in FIG. 4B, the transparent substrate 10 of the EC element 1 may be considered as the transparent plate 113, for example.

Such a dimming window is applicable to application of adjusting the incident amount of sunlight into a room at daytime, for example. Since the dimming window is applicable to adjustment of a heat amount other than the amount of sunlight, it can be used for controlling the brightness or the temperature of a room. Further, the dimming window is applicable as a shutter to application for shielding landscape from the outdoor to the indoor. Such a dimming window is applicable to a window of a vehicle such as an automobile, a train, an airplane, or a ship other than a glass window for a building.

As discussed above, the EC element 1 including the organic compound expressed by general formula (1) in the EC layer 12 can be used in an optical filter, a lens unit, an imaging apparatus, a window member, or the like. Each of the optical filter, the lens unit, the imaging apparatus, and the window member of the present embodiment can provide various absorption color with the organic compound expressed by general formula (1) alone or in combination with an EC compound having coloring absorption in another wavelength band. Further, since each of the optical filter, the lens unit, the imaging apparatus, and the window member of the present embodiment includes the organic compound expressed by general formula (1), the transparency in an achromatized state can be improved.

EXAMPLES

While the present invention will be more specifically described below with examples, the present invention is not limited thereto.

Example 1 (Synthesis of Example Compound A-3)

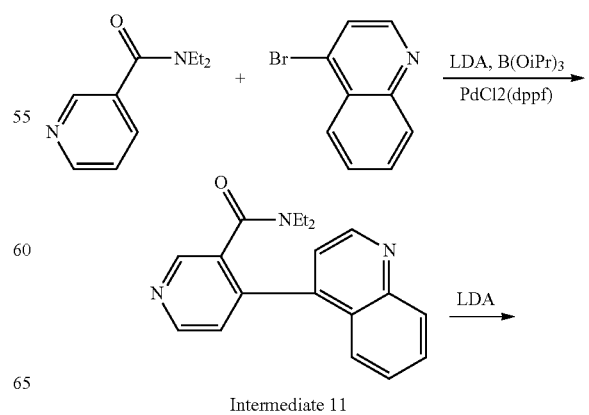

Intermediate 11

-continued

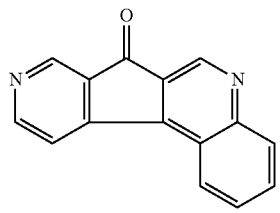

Intermediate 12

Tetrahydrofuran (80 ml) and diisopropylamine (16 ml, 110 mmol) were added in a reactor, and the mixture was cooled to −70 degrees Celsius. After 1.6M butyllithium hexane solution (70 ml, 110 mmol) was gradually dropped into the solution, the temperature was increased to 0 degree Celsius, and an LDA solution was prepared. In addition, N,N-diethylnicotinamide (18 g, 100 mmol), triisopropyl borate (25 ml, 110 mmol), and tetrahydrofuran (80 ml) were prepared, and the mixture was cooled to −10 degrees Celsius. After the LDA solution prepared in advance was gradually dropped into the solution and the solution was stirred for two hours at the room temperature, [1,1'-bis (diphenylphosphino)ferrocene]palladium(II)dichloride dichloromethane adduct (1.7 g, 2 mmol), 4-bromoquinoline (13.7 g, 66 mmol), tetrahydrofuran (160 ml), potassium phosphate (139 g, 250 mmol), and water (150 ml) were added thereto, and the solution was stirred for 14 hours at 60 degrees Celsius. After a relation solution was left at the room temperature, Celite filtration and extraction with ethyl acetate were performed. The extracted product was dried with anhydrous sodium sulfate and condensed, and a brown solid was yielded. This was column-purified (eluent: hexane/ethyl acetate=1/2), and a yellow solid intermediate 11 was yielded (16 g, yield: 80%).

Tetrahydrofuran (40 ml) and diisopropylamine (8 ml, 55 mmol) were added in a reactor, and the mixture was cooled to −70 degrees Celsius. After 1.6M butyllithium hexane solution (35 ml, 55 mmol) was gradually dropped into the solution, the temperature was increased to 0 degree Celsius, and an LDA solution is prepared. After tetrahydrofuran solution (40 ml) of the intermediate 11 (15 g, 50 mmol) was gradually dropped into the solution, the temperature was increased to the room temperature, and the solution was stirred for 16 hours. After a saturated ammonium chloride solution was added, and the solution was stirred for 30 minutes, crystals yielded by filtration was washed sequentially with water and methanol, and a gray powder intermediate 12 was yielded (7.4 g, yield: 64%).

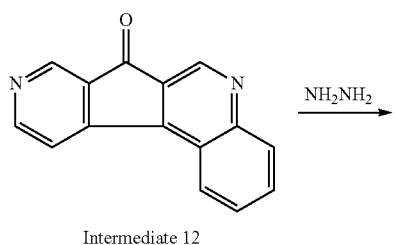

Intermediate 12

-continued

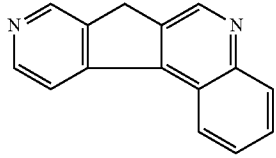

Intermediate 13

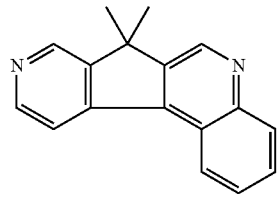

Intermediate 14

The intermediate 12 (4.6 g, 20 mmol), 1-butanol (70 mL), and hydrazine monohydrate (10 ml, 200 mmol) were added in a reactor and stirred at 100 degrees Celsius for 12 hours. After cooling, water was added to this solution and then condensed, a solid was yielded. This was column-purified (eluent: ethyl acetate/methanol=10/1), and a light brown solid intermediate 13 was yielded (2.8 g, yield: 64%).

The intermediate 13 (2.2 g, 10 mmol) and N,N-dimethyl formamide (15 mL) were added in a reactor, and the mixture was cooled to 5 degrees Celsius in an ice bath. After potassium tert-butoxide (2.2 g, 20 mmol) was added to the solution, the solution was stirred for 30 minutes at the same temperature, and iodomethane (3.1 g, 22 mmol) diluted in N,N-dimethyl formamide (5 mL) was dropped into the solution. After the solution was stirred for 30 minutes at the same temperature, the cooling bath was removed, the solution was stirred for 3 hours under the room temperature. A saturated sodium bicarbonate water was added to the reacted liquid, extraction was performed with ethyl acetate, an organic phase was mixed, the mixture was washed sequentially with water and saturated salt water, and the mixture was dried with anhydrous sodium sulfate and condensed, and a black-yellow solid was yielded. This was column-purified (eluent: ethyl acetate/methanol=10/1), and a beige solid intermediate 14 was yielded (150 mg, yield: 3%).

The intermediate 14 (98 mg, 0.4 mmol), 1-iodoheptane (203 mg, 0.9 mmol), and DMF (10 ml) were prepared in a reactor, and the solution was stirred for 8 hours under a heat reflux. After the end of the reaction, precipitated crystal was filtrated and washed with acetonitrile, and 223 mg of an exemplary compound A-3 was yielded (yield: 80%).

The structure of the compound A-3 was confirmed by NMR measurement. $^1$H NMR (DMSO-d6, 500 MHz), σ (ppm): 10.22 (s, 1H), 9.81 (s, 1H), 9.48 (d, 1H), 9.41 (d, 1H), 9.31 (d, 1H), 8.82 (d, 1H), 8.40 (t, 1H), 8.27 (t, 1H), 5.17 (t, 2H), 4.74 (t, 2H), 2.06 (m, 4H), 1.79 (s, 6H), 1.50-1.22 (m, 16H), 0.87 (m, 6H).

Example 2 (Synthesis of Example Compound A-2)

The exemplary compound A-3 (210 mg, 0.3 mmol) was solved in water. A solution in which 500 mg of potassium hexafluorophosphate was solved was dropped, and the solution was stirred for 3 hours at the room temperature. Precipitated crystal was filtrated and washed sequentially with isopropylalcohol and diethylether, and 212 mg of an exemplary compound A-2 was yielded (yield: 96%).

The structure of the compound A-2 was confirmed by NMR measurement. $^1$H NMR (DMSO-d6, 500 MHz), σ (ppm): 10.22 (s, 1H), 9.81 (s, 1H), 9.48 (d, 1H), 9.41 (d, 1H), 9.31 (d, 1H), 8.82 (d, 1H), 8.40 (t, 1H), 8.27 (t, 1H), 5.17 (t, 2H), 4.74 (t, 2H), 2.06 (m, 4H), 1.79 (s, 6H), 1.50-1.22 (m, 16H), 0.87 (m, 6H).

Example 3 (Fabrication of Electrochromic Element and Evaluation of Characteristics)

Tetrabutylammonium perchlorate as an electrolyte was solved at a concentration of 0.1 M in propylene carbonate, then the exemplary compound A-2 of Example 2 was solved at a concentration of 40.0 mM, and an EC medium was yielded. Next, insulating layers (SiO$_2$) were formed at the end of four corners of a pair of glass substrates with a transparent conductive film (ITO). A PET film used for defining a distance between the substrates (Teijin DuPont Films Japan Limited, Melinex (registered trademark) S, 125 μm thickness) was arranged between the pair of glass substrates with transparent electrode films. Then, the substrates and the PET film were adhered by an epoxy-based adhesive agent except the inlet used for injecting the EC medium and sealed. As discussed above, an empty cell with the inlet was fabricated. Next, after the EC medium yield in the above process was injected by a vacuum injection method, the inlet was sealed by an epoxy-based adhesive agent, and an EC element was resulted.

Figure 5:
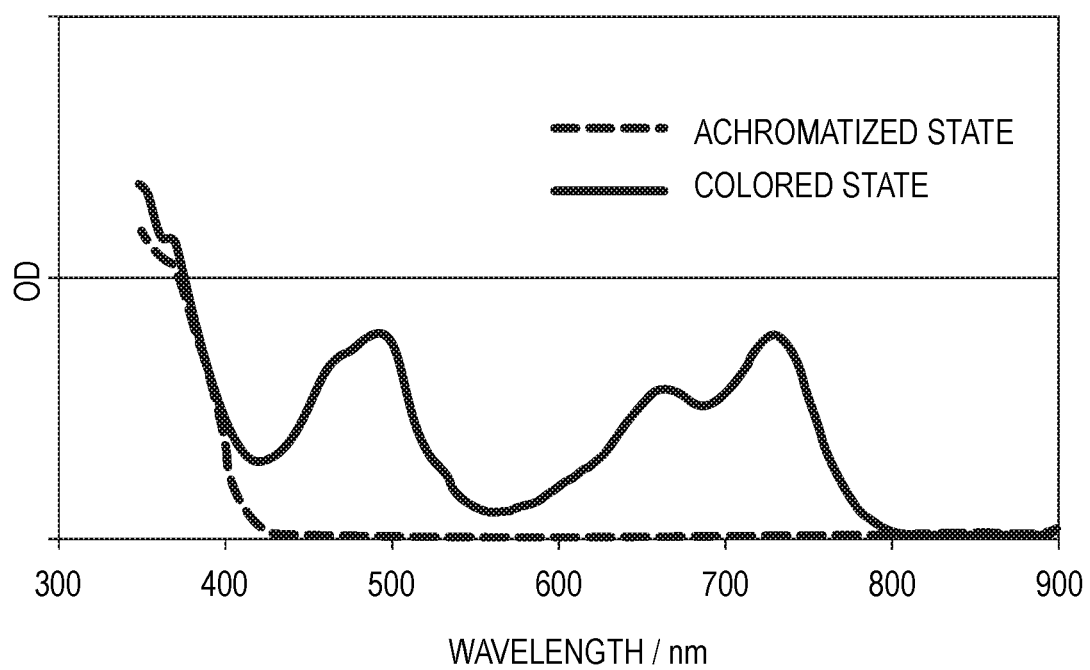
FIG. 5 is an ultraviolet visible absorption spectral of a colored state and an achromatized state of an electrochromic element of Example 3.

The EC element resulted immediately after the fabrication exhibited a transmittance around 80% and thus had a high transparency over the entire visible light range. When a voltage of 2.0 V was applied to this element, absorption due to reduced species of the exemplary compound A-2 (λmax=490 nm) was exhibited, and the element was colored. Moreover, application of –0.5 V caused achromatizing. This element is reversibly changeable between a colored state and an achromatized state. FIG. 5 is an ultraviolet visible absorption spectral of the element fabricated in the present example. As a light source, DH-2000S deuterium halogen light source by Ocean Optics, Inc. was used.

Example 4 (Synthesis of Example Compound A-42)

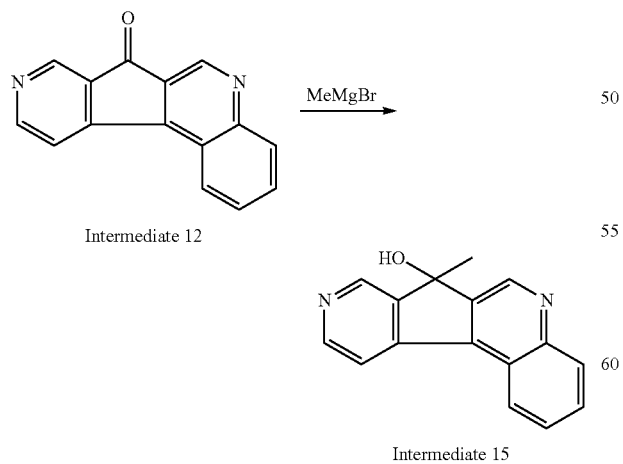

Intermediate 12

Intermediate 15

The intermediate 12 (697 mg, 3 mmol) and THF (9 mL) were prepared in a reactor under a nitrogen flow. After the mixture was cooled to –5 degrees Celsius, methylbromomagnesium (approximately, 1M, THF solution) (12 ml) was dropped over around five minutes, and the solution was stirred for one hour. After the end of the reaction, 2M hydrochloric acid (5 mL) was dropped, 10M sodium hydroxide (5 mL) was then added. The precipitate was filtrated out by filtration under reduced pressure and washed by ethylacetate, and an aqueous phase was further extracted twice by ethylacetate. An organic phase was condensed and column-purified, and thereby an intermediate 15 was yielded as powders in the reactor (534 mg, yield: 72%).

The intermediate 15 (99 mg, 0.4 mmol), 1-iodeheptan (452 mg, 2.0 mmol), and acetonitrile (10 ml) were prepared in the reactor, the solution was stirred for 48 hours under heated to reflux. After the end of the reaction, the deposited crystal was filtrated, and washed by acetonitrile. The yielded crystal was solved in water. A solution in which ammonium hexafluorophosphate (500 mg) was solved was dropped, and the solution was stirred for three hours at the room temperature. The deposited crystal was filtrated and re-crystallized with propanol/diisopropyl ether, and thereby 118 mg of an exemplary compound A-42 was yielded (yield: 40%).

The structure of the compound A-42 was confirmed by NMR measurement.

$^1$H NMR (DMSO-d6, 500 MHz), σ (ppm): 10.12 (s, 1H), 9.66 (s, 1H), 9.42 (m, 2H), 9.26 (d, 1H), 8.82 (d, 1H), 8.42 (t, 1H), 8.26 (t, 1H), 5.22 (m, 2H), 4.76 (t, 2H), 2.13 (m, 4H), 1.96 (s, 3H), 1.50-1.21 (m, 16H), 0.85 (m, 6H).

Example 5 (Production and Characteristics Evaluation of Electrochromic Element)

Figure 6:
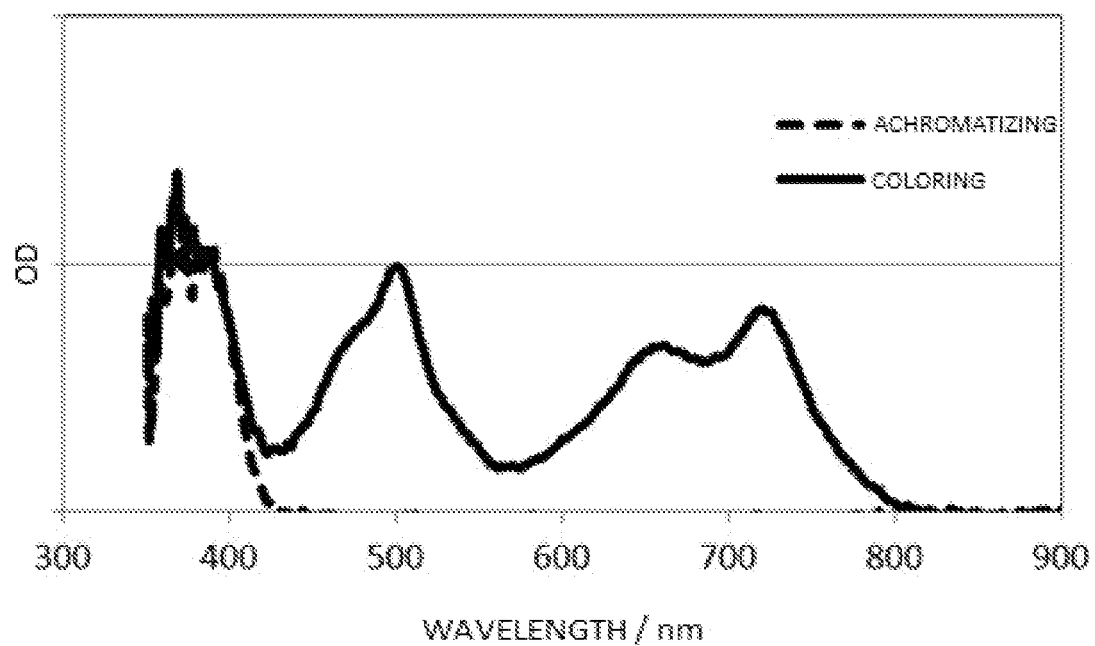
FIG. 6 is an ultraviolet visible absorption spectral of a colored state and an achromatized state of an electrochromic element of Example 5.

In Example 3, an element was produced by the same method as in Example 3 except that the exemplary compound A-42 was used instead of the exemplary compound A-2. When a voltage of 2.0 V was applied to an element of the present example, absorption based on reduction species of the exemplary compound A-42 (λmax=501 nm) was exhibited. Furthermore, a voltage of –0.5 V was applied, the element was achromatized, and reversible coloring and achromatizing was exhibited. The color spectral is illustrated in FIG. 6.

Example 6 (Synthesis of Example Compound A-45)

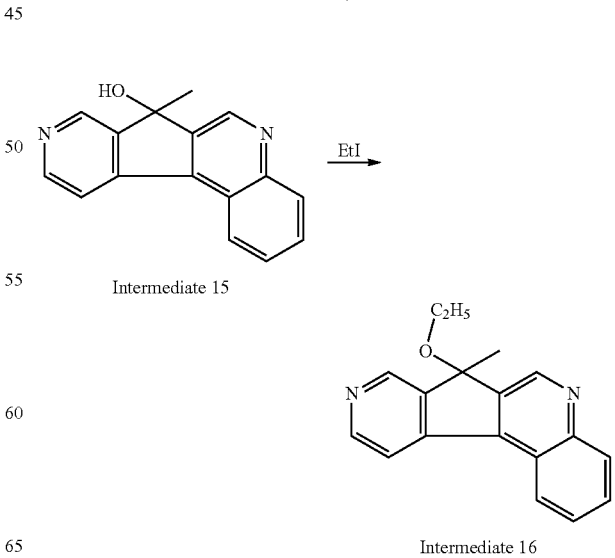

Intermediate 15

Intermediate 16

A DMF (10 mL) and sodium hydroxide (85 mg, 2.1 mmol) were prepared in a reactor under a nitrogen flow. After the mixture was cooled to 0 degrees Celsius, a DMF solution of the intermediate 15 (420 mg, 1.7 mmol) was dropped. After the solution was stirred for 30 minutes, EtI (ethyliodide) (316 mg, 2.0 mmol) was slowly added, the temperature was increased to a room temperature, and the solution was stirred for 12 hours. After the end of the reaction, a saturated saline solution was added, and the extraction was performed by ethylacetate. An organic phase was condensed and column-purified, and thereby an intermediate 16 was yielded as powders in the reactor (360 mg, yield: 77%).

The intermediate 16 (110 mg, 0.4 mmol), dichloromethane (5 ml), and acetonitrile (5 ml) were prepared in a reactor, trimethyloxonium tetrafluoroborate (473 mg, 3.2 mmol) was added under a nitrogen flow, and the solution was stirred for 12 hours. After the end of the reaction, isopropylether was added, and a crystal was yielded. The yielded crystal was solved in water, a solution in which ammonium hexafluorophosphate (500 mg) was solved was dropped, and the solution was stirred for three hours at the room temperature. The deposited crystal was filtrated and re-crystalized with acetonitrile/diisopropylether, and thereby 131 mg of the exemplary compound A-45 was yielded (yield: 55%).

The structure of the compound A-45 was confirmed by NMR measurement.

$^1$H NMR (DMSO-d6, 500 MHz), σ (ppm): 10.07 (s, 1H), 9.58 (s, 1H), 9.44 (d, 1H), 9.38 (d, 1H), 9.27 (d, 1H), 8.72 (d, 1H), 8.45 (m, 1H), 8.28 (t, 1H), 4.78 (s, 3H), 4.51 (s, 3H), 3.51 (q, 4H), 1.92 (s, 3H), 1.06 (t, 3H).

Example 7 (Production and Characteristics Evaluation of Electrochromic Element)

Figure 7:
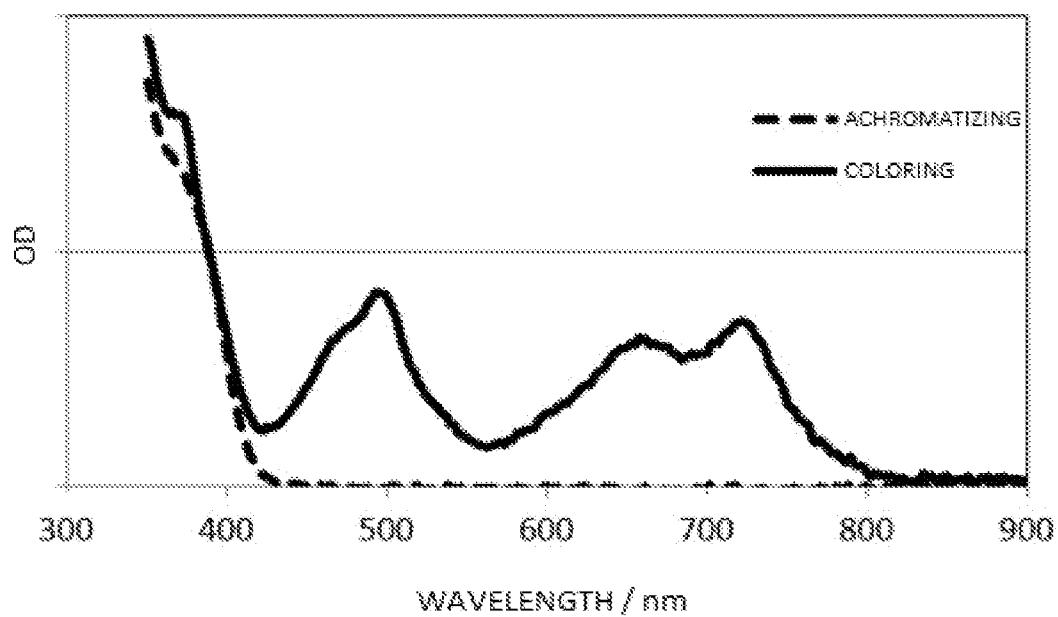
FIG. 7 is an ultraviolet visible absorption spectral of a colored state and an achromatized state of an electrochromic element of Example 7.

In Example 3, an element was produced by the same method as in Example 3 except that the exemplary compound A-45 was used instead of the exemplary compound A-2. When a voltage of 2.0 V was applied to an element of the present example, absorption based on reduction species of the exemplary compound A-45 (λmax=495 nm) was exhibited. Furthermore, a voltage of −0.5 V was applied, the element was achromatized, and reversible coloring and achromatizing was exhibited. The color spectral is illustrated in FIG. 7.

Example 8 (Synthesis of Example Compound A-41)

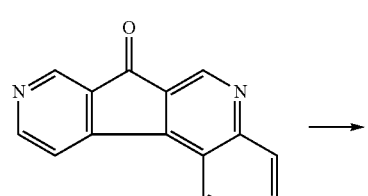

Intermediate 12

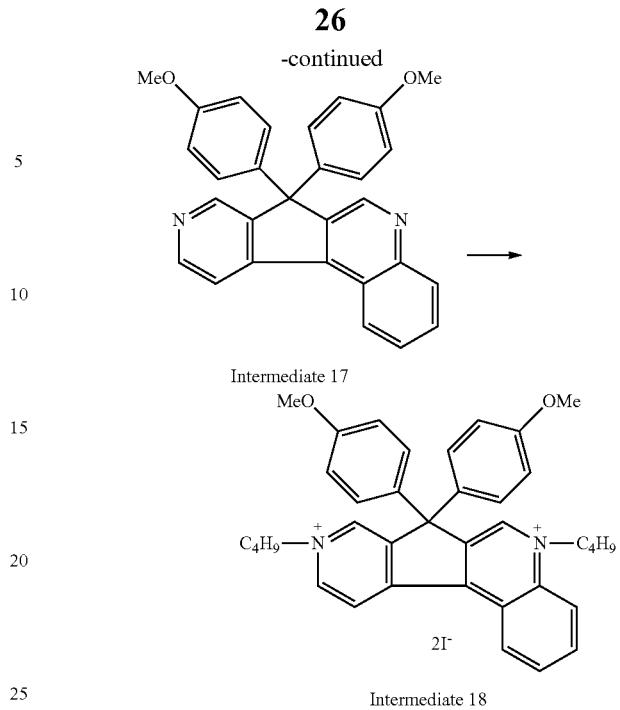

Intermediate 17

Intermediate 18

The intermediate 12 (241 mg, 1.04 mmol), anisole (1.2 mL), and 3-mercaptopropionic acid (0.9 μl, 0.01 mmol) were added in a reactor. After the mixture was cooled to 0 degree Celsius, concentrated sulfuric acid (0.6 ml) was dropped, and the solution was heated and stirred for five hours at 70 degrees Celsius. A sodium hydroxide solution was added to the solution after cooled, and thereby the reaction system became alkaline. Water was added to the solution, the solution was subjected to extraction with chloroform and then condensed, and thereby a solid was yielded. This was column-purified (eluent: hexane/chloroform), and an intermediate 17 as a light yellow solid was yielded (310 mg, yield: 69%).

The intermediate 17 (270 mg, 0.63 mmol), 1-iodobutane (1.15 g, 6.3 mmol), and 2-methoxyethanol (1 mL) were added in a reactor, and the solution was stirred for 24 hours at 100 degrees Celsius. After cooled, ethylacetate was added, a deposited solid was filtrated and further washed with ethylacetate, and an intermediate 18 was yielded (240 mg, yield: 48%).

The intermediate 18 (240 mg, 0.3 mmol) was solved in water. A solution in which ammonium hexafluorophosphate (200 mg) was solved was dropped, and the solution was stirred for three hours at the room temperature. The deposited crystal was filtrated and washed sequentially with isopropylalcohol and diethylether, and 212 mg of the exemplary compound A-41 was yielded (yield: 85%).

The structure of the compound A-41 was confirmed by NMR measurement.

$^1$H NMR (CD3CN, 500 MHz), δ (ppm): 9.31 (s, 1H), 9.12 (d, 1H), 9.08 (d, 1H), 8.98 (s, 1H), 8.97 (d, 1H), 8.58 (d, 1H), 8.39 (t, 1H), 8.30 (t, 1H), 7.25 (d, 4H), 6.93 (d, 4H), 5.01 (t, 2H), 4.61 (t, 1H), 3.80 (s, 6H), 2.02 (m, 4H), 1.37 (m, 4H), 0.96 (t, 3H), 0.94 (t, 3H).

Example 9 (Production and Characteristics Evaluation of Electrochromic Element)

In Example 3, an element was produced by the same method as in Example 3 except that the exemplary compound A-41 was used instead of the exemplary compound A-2. When a voltage of 2.0 V was applied to an element of the present example, absorption based on reduction species of the exemplary compound A-41 (λmax=505 nm) was exhibited. Furthermore, a voltage of −0.5 V was applied, the element was achromatized, and reversible coloring and achromatizing was exhibited.

According to the present invention, an organic compound that can absorb a light of a range around 500 nm to be colored or achromatized by oxidation-reduction reaction and has a high stability against repeated oxidation-reduction reaction can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-019294, filed Feb. 6, 2018, and Japanese Patent Application No. 2019-004490, filed Jan. 15, 2019, which are hereby incorporated by reference herein in their entirety.

What is claimed is:

1. An organic compound represented by a following general formula (1):

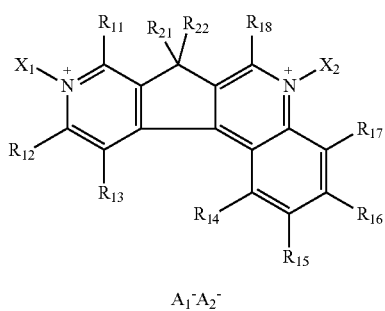

wherein, in the general formula (1), $X_1$ and $X_2$ are independently selected from the group consisting of a substituted or unsubstituted alkyl group, a substituted or unsubstituted aryl group, and a substituted or unsubstituted aralkyl group, $R_{11}$ to $R_{18}$ are independently selected from the group consisting of a hydrogen atom and a substituent, and each substituent represented by the $R_{11}$ to $R_{18}$ is any one of a substituted or unsubstituted alkyl group, a substituted or unsubstituted alkoxy group, a substituted or unsubstituted aryl group, a substituted or unsubstituted heterocyclic group, a halogen atom, and a cyano group, $R_{21}$ and $R_{22}$ are independently selected from the group consisting of a hydrogen atom and a substituent, and each substituent represented by the $R_{21}$ and $R_{22}$ is any one of a substituted or unsubstituted alkyl group, a substituted or unsubstituted aryl group, and a substituted or unsubstituted aralkyl group, and $A_1^-$ and $A_2^-$ independently represent a monovalent anion.

2. The organic compound according to claim 1, wherein the $A_1^-$ and the $A_2^-$ are the same anion.

3. An electrochromic element comprising:
a pair of electrodes; and
an electrochromic layer arranged between the pair of electrodes, the electrochromic layer containing the organic compound according to claim 1.

4. The electrochromic element according to claim 3, wherein the electrochromic layer has another type of organic compound that is of a different type from the organic compound.

5. The electrochromic element according to claim 4, wherein the another type of organic compound is any one of a phenazine compound, a metallocene compound, and a phenylenediamine compound, and a pyrazoline compound.

6. The electrochromic element according to claim 3, wherein the electrochromic layer is a liquid having an electrolyte and the organic compound.

7. An optical filter comprising:
an electrochromic element according to claim 3; and
an active element connected to the electrochromic element.

8. The optical filter according to claim 7, wherein the active element is an active element that drives the electrochromic element and adjusts an amount of a light passing through the electrochromic element.

9. A lens unit comprising:
the optical filter according to claim 7; and
an imaging optical system having a plurality of lenses.

10. An imaging apparatus comprising:
an imaging optical system having a plurality of lenses;
the optical filter according to claim 7; and
an imaging device that receives a light that has passed through the optical filter.

11. The imaging apparatus from which an imaging optical system having a plurality of lenses is removable, the imaging apparatus comprising:
the optical filter according to claim 7; and
an imaging device that receives a light that has passed through the optical filter.

12. A window member comprising:
the electrochromic element according to claim 3; and
an active element connected to the electrochromic element.

13. The window member according to claim 12, wherein the active element is an active element that drives the electrochromic element and adjusts an amount of a light passing through the electrochromic element.

* * * * *